(12) United States Patent
Kato et al.

(10) Patent No.: US 7,060,656 B2
(45) Date of Patent: Jun. 13, 2006

(54) ANTIBACTERIAL ROCKWOOL GROWTH MEDIUM FOR HYDROPONICS

(75) Inventors: Yoshinari Kato, Mizunami (JP); Satoshi Kameshima, Mizunami (JP)

(73) Assignee: Akechi Ceramics Kabushiki Kaisha, Gifu (JP)

( * ) Notice: Subject to any disclaimer, the term of this patent is extended or adjusted under 35 U.S.C. 154(b) by 272 days.

(21) Appl. No.: 10/738,227

(22) Filed: Dec. 17, 2003

(65) Prior Publication Data

US 2004/0131699 A1    Jul. 8, 2004

(30) Foreign Application Priority Data

Dec. 20, 2002  (JP)  ............................ 2002-369711

(51) Int. Cl.
- *A01N 59/16* (2006.01)
- *A01N 59/20* (2006.01)
- *A01N 25/08* (2006.01)
- *A01G 31/00* (2006.01)
- *C05D 9/02* (2006.01)

(52) U.S. Cl. ...................... 504/101; 504/187; 504/358; 47/59 R; 47/62 N; 47/62 R; 47/64; 71/31; 71/62; 71/904; 424/409; 424/411; 424/618; 424/629; 424/630; 424/638

(58) Field of Classification Search ................ 504/187, 504/358, 101; 47/62 R, 62 N, 59 R, 64; 71/31, 62, 904; 424/409, 411, 618, 629, 424/630, 638
See application file for complete search history.

(56) References Cited

FOREIGN PATENT DOCUMENTS

JP            63-52827           3/1988

OTHER PUBLICATIONS

Duffy, B.K. et al., "Environmental signals in biocontrol of tomato root disease by Pseudomonas fluorescens". Retrieved from STN Database accession No. 1998-82262 XP002278890, Cropu Abstract, 1998.

Sheen, T.F. et al., "Effect of different rockwool culture methods on root temperature of greenhouse muskmelon". Retrieved from STN Database accession No. 1998:26573 XP 002278891 (1998).

*Primary Examiner*—John Pak
(74) *Attorney, Agent, or Firm*—Koda & Androlia

(57) ABSTRACT

An antibacterial rockwool growth medium for hydroponics is used for hydroponic growth of rice, flowers and ornamental plants, fruitage, etc. The medium includes a rockwool base used as a culture medium for hydroponics, and an inorganic antibacterial agent is dispersed substantially uniformly onto an overall surface of the rockwool base or a part of the surface of the rockwool base.

1 Claim, 1 Drawing Sheet

ANTIBACTERIAL ROCKWOOL GROWTH MEDIUM FOR HYDROPONICS

BACKGROUND OF THE INVENTION

1. Field of the Invention

This invention relates to an antibacterial rockwool growth medium for hydroponics used for hydroponic growth of rice, flowers and ornamental plants, fruitage, etc.

2. Description of the Related Art

In hydroponics, measures against bacteria in which a nutrient solution primarily serves as a medium include addition of agricultural chemicals, disinfection by addition of hypochlorous acid, disinfection by antibacterial metal ion such as eluted silver or copper, high temperature sterilization and disinfection by ozone. In the disinfection by the eluted metal ion, a metal ion is eluted in a nutrient solution to displace a sulfhydryl group (—SH) possessed by bacteria, whereby the bacteria is deactivated. Furthermore, when added into the nutrient solution of hydroponics, agricultural chemical, chlorine, or ion such as silver or copper has a quick-acting property and is accordingly effective. However, there is a possibility that plant roots may be damaged by chemical injury. Moreover, since the effect of the foregoing method is not persistent, an antibacterial or bactericidal component in the nutrient solution needs to be continuously controlled. In the high temperature sterilization or ozonic disinfection, an aseptic condition can be maintained for a short period of time after the treatment, but almost no disinfection effect can be achieved near the plant root when bacteria invade the nutrient solutions during subsequent circulation.

A rockwool base used for the hydroponics is sterilized at the time of completion of manufacture since it is sintered at 200° C. to 300° C. at a final manufacturing step. Accordingly, once invading the rockwool base, bacteria rapidly propagate themselves such that the rockwool base is contaminated by the bacteria. Replanting is impossible in the use of the contaminated rockwool culture medium. Thus, a plant growing method in which disinfection can reliably take place near the plant root has been desired.

SUMMARY OF THE INVENTION

Therefore, an object of the present invention is to provide an antibacterial rockwool growth medium for hydroponics in which propagation of bacteria can be restrained in the rockwool and accordingly which has an improved antibacterial effect.

To achieve the object, the present invention provides an antibacterial rockwool growth medium for hydroponics comprising a rockwool base used as a culture medium for hydroponics, wherein an inorganic antibacterial agent is dispersed substantially uniformly onto an overall surface thereof or a part of the surface thereof.

Propagation of bacteria is restrained near plant roots since the inorganic antibacterial agent is dispersed substantially uniformly onto the overall surface thereof or a part of the surface thereof, whereupon the rockwool growth medium of the invention provides a reliable measure against bacteria. Consequently, replanting can be carried out with use of the same rockwool growth medium. Furthermore, since no antibacterial and/or bactericidal component such as agricultural chemicals needs to be added to nutrient solutions, the rockwool growth medium is maintenance free and can continuously provide an antibacterial effect when once installed.

In one embodiment of the invention, the inorganic antibacterial agent comprises silver and/or copper and a metal component of the inorganic antibacterial agent has an amount of elution into a nutrient solution not more than 50 ppb and is dispersed so as to range from 0.01 to 5.0 wt. % relative to the rockwool base. Consequently, the nutrient solution contains little silver ion and/or copper ion each having antibacterial properties, whereupon stable antibacterial effects can be maintained for a long time. Furthermore, the inorganic antibacterial agent is also effective on fungi since it contains copper. Additionally, waste liquid resulting from replacement of liquid is clean and accordingly has no adverse effect on the environment.

Roots are easily damaged by chemicals and an adverse effect on the environment is increased when an amount of eluting metal component exceeds 50 ppb. When the metal component such as silver or copper having antibacterial properties against the rockwool growth medium is less than 0.01 wt. %, a contact area of bacteria and a metal component in the nutrient solution is small such that bacteria cannot easily be extinct instantaneously. On the other hand, when the metal component exceeds 5.0 wt. %, the antibacterial effect is increased but the rockwool growth medium is discolored or the water retention of the medium is reduced.

BRIEF DESCRIPTION OF THE DRAWINGS

Other objects, features and advantages of the present invention will become clear upon reviewing the following description of the embodiment with reference to FIG. 1 showing a simplified hydroponic growing apparatus to which the antibacterial rockwool growth medium for hydroponics in accordance with the present invention is applied.

DETAILED DESCRIPTION OF THE INVENTION

Embodiment 1

Figure 1:
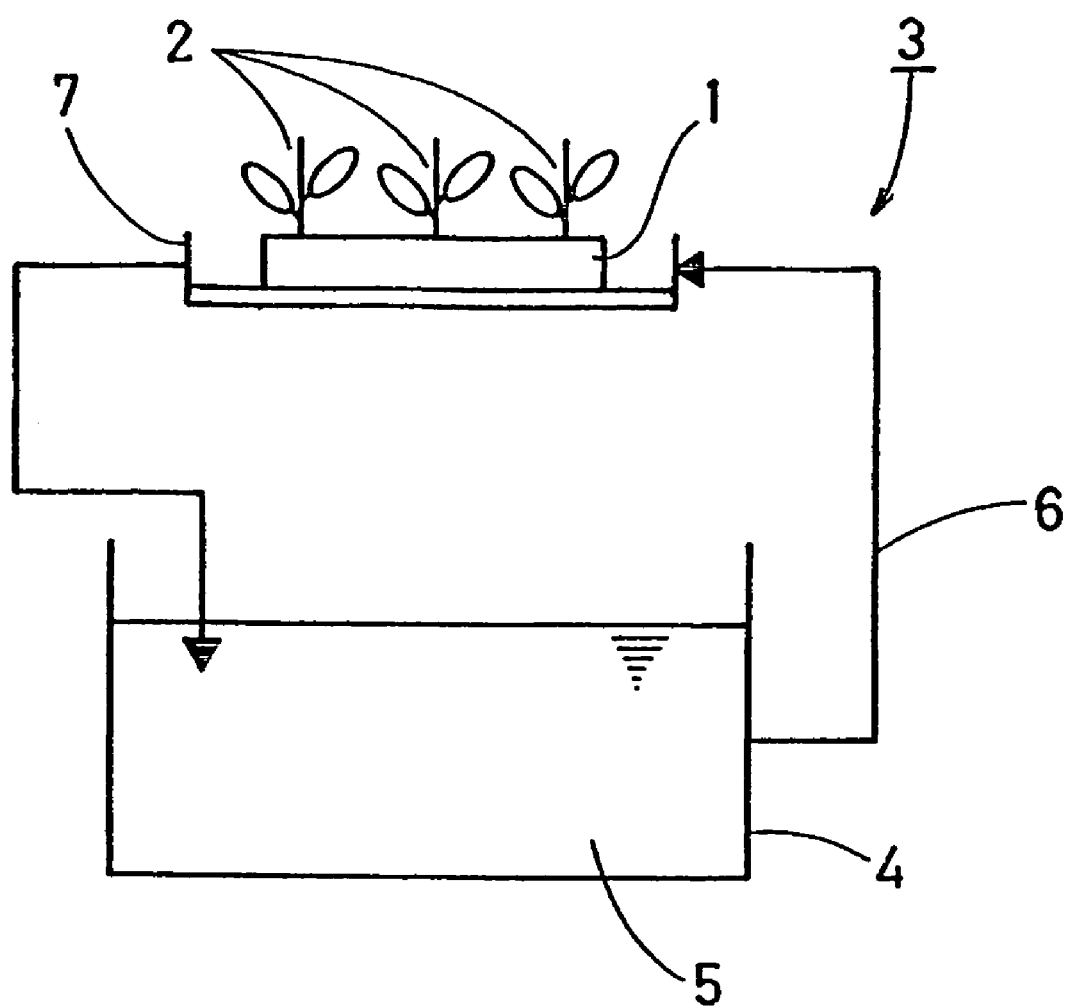

Reference numeral 1 designates an antibacterial rockwool growth medium for hydroponics in accordance with one embodiment of the present invention. The antibacterial rockwool growth medium 1 is made as follows. An inorganic silver antibacterial agent 10 g, whose amount of elution into a liquid is not more than 50 ppb, is kneaded together with phenol resin 100 g as an organic binder so that a ratio of the antibacterial agent to a rockwool base used as a growth medium becomes 0.2 wt. %. The kneaded material is sprayed over the surface of fiber composing the rockwool base so as to be dispersed substantially uniformly. Thereafter, the base 1a is formed into a shape of 300 mm×300 mm×75 mm and then dried at 200° C. thereby to be hardened.

An evaluation experiment was conducted. In the experiment, the antibacterial rockwool growth medium 1 was planted with three roots of a miniature rose 2. The miniature rose 2 was grown by a simplified hydroponic growing apparatus 3 for 20 days. As shown in the figure, the simplified hydroponic growing apparatus 3 was comprised of a tank 4 storing a nutrient solution 5 for hydroponics and a circulation piping 6 circulating the nutrient solution 5 via a growing bed 7 on which the antibacterial rockwool growth medium 1 was set. The nutrient solution 5 in circulation was periodically inoculated with helicoid zoospore in order that occurrence of diseases might be examined. Furthermore, an eluted component in the circulated nutrient solution 5 was measured by fluorescent X ray.

Embodiment 2

Embodiment 2 is the same as the above-described embodiment 1 except that a content of silver and copper is 1:1 in the used inorganic silver-copper antibacterial agent.

COMPARED EXAMPLE 1

Sodium hypochlorite is added into the nutrient solution only during planting so that a concentration of chlorine in the nutrient solution becomes 4 ppm. The used rockwool base is untreated. The evaluating manner in compared example 1 was the same as in embodiment 1.

COMPARED EXAMPLE 2

An inorganic silver antibacterial agent 0.1 g was kneaded together with phenol resin 100 g so that a ratio of the antibacterial agent to a rockwool base used as a growth medium became 0.002 wt. %. The kneaded material was sprayed over the surface of fiber composing the rockwool base so as to be dispersed substantially uniformly. The rockwool growth medium of compared example 2 was the same as embodiments 1 and 2 in the other respects and evaluated in the same manner as embodiments 1 and 2.

COMPARED EXAMPLE 3

An inorganic silver antibacterial agent 300 g was kneaded together with phenol resin 100 g so that a ratio of the antibacterial agent to a rockwool base used as a growth medium became 6.0 wt. %. The kneaded material was sprayed over the surface of fiber composing the rockwool base so as to be dispersed substantially uniformly. The rockwool growth medium of compared example 3 was the same as embodiments 1 and 2 in the other respects and evaluated in the same manner as embodiments 1 and 2.

COMPARED EXAMPLE 4

A silver ion eluting inorganic silver antibacterial agent 10 g was kneaded together with phenol resin 100 g. The kneaded material was sprayed over the surface of fiber composing the rockwool base so as to be dispersed substantially uniformly. The rockwool growth medium of compared example 4 was the same as each embodiment in the other respects and evaluated in the same manner as each embodiment.

TABLE 1 shows the results of occurrence of diseases in the above-described evaluation experiments. No diseases occurred in the three roots of rose in examples 1 and 2 and compared example 3. However, the roots of rose in each of embodiments 1 and 2 were 14 cm high, whereas the roots of rose in compared example 3 were 8, 7 and 6 cm respectively, which values were about one half of those of each embodiment. Furthermore, no fungi were found in embodiment 2 using the silver-copper compound antibacterial agent, whereby fungus resistance was observed.

TABLE 1

| | Occurrence of Diseases (20 days after) | Height |
|---|---|---|
| Example 1 | No diseases in 3 seedlings | 15 cm, 15 cm and 14 cm |
| Example 2 | No diseases in 3 seedlings | 15 cm, 16 am and 15 cm |
| Compared Embodiment 1 | Diseases found in each of 3 seedlings | Not measured |
| Compared Embodiment 2 | Diseases found in each of 3 seedlings | Not measured |
| Compared Embodiment 3 | No diseases in 3 seedlings | 8 cm, 7 cm and 6 cm |
| Compared Embodiment 4 | Diseases found in 2 seedlings | Not measured in 2 seedlings and 6 cm in the other |

As obvious from the results shown in TABLE 1, there is a high possibility of occurrence of diseases in the case where the metal component of silver and copper in each of which antibacterial properties against the rockwool growth medium is less than 0.01 wt. %. Furthermore, the results show that plant growing is adversely affected when the metal component exceeds 5 wt. %.

TABLE 2 shows the results of the experiment in which the eluted component in the nutrient solution 5 in circulation was measured by fluorescent X ray. The elution of silver ion was at or below 0.001 ppm in all the embodiments and compared examples except compared example 4.

TABLE 2

| | Eluted component in ppm | | | | |
|---|---|---|---|---|---|
| | Ag | Cu | Li | Na | Ca |
| Embodiment 1 | <0.001 | <0.001 | 0.0024 | 8.81 | 56.37 |
| Embodiment 2 | <0.001 | <0.001 | 0.0021 | 8.74 | 56.11 |
| Compared Example 1 | <0.001 | <0.001 | 0.0037 | 7.97 | 56.49 |
| Compared Example 2 | <0.001 | <0.001 | 0.0035 | 7.92 | 56.15 |
| Compared Example 3 | <0.001 | <0.001 | 0.0039 | 7.89 | 56.78 |
| Compared Example 4 | 1.97 | <0.001 | 0.0097 | 5.97 | 50.89 |

As obvious from TABLE 2, the silver ion elutes from the silver ion eluting antibacterial agent. It is obvious from TABLE 1 that the eluted ion adversely affected plant growth.

As obvious from the foregoing, the antibacterial rockwool growth medium 1 of the present invention can restrain propagation of bacteria present in the nutrient solution for hydroponics. Furthermore, even when bacteria is present in the rockwool growth medium, the bacteria can be extinct such that the bacteria are not released into the nutrient solution. Additionally, the antibacterial rockwool growth medium of the present invention can remain effective against bacteria such as red stele for a long time.

The foregoing description and drawings are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

We claim:

1. An antibacterial rockwool growth medium for hydroponics comprising a rockwool base used as a culture medium for hydroponics, wherein an inorganic antibacterial agent is dispersed substantially uniformly onto an overall surface thereof or a part of the surface thereof the inorganic antibacterial agent comprises silver and/or copper and a metal component of the inorganic antibacterial agent has an amount of elution into a nutrient solution not more than 50 ppb and is dispersed so as to range from 0.01 to 5.0 wt. % relative to the rockwool base.

* * * * *